United States Patent
Humele

(10) Patent No.: US 9,272,060 B2
(45) Date of Patent: Mar. 1, 2016

(54) METHOD FOR PRE-TREATING PREFORMS AND BLOW MOLDING APPARATUS FOR PRE-TREATING AND BLOW MOLDING PREFORMS INTO CONTAINERS

(75) Inventor: Heinz Humele, Thalmassing (DE)

(73) Assignee: Krones AG, Neutraubling (DE)

( * ) Notice: Subject to any disclaimer, the term of this patent is extended or adjusted under 35 U.S.C. 154(b) by 83 days.

(21) Appl. No.: 13/102,266

(22) Filed: May 6, 2011

(65) Prior Publication Data

US 2011/0272861 A1  Nov. 10, 2011

Related U.S. Application Data

(63) Continuation of application No. PCT/EP2009/062532, filed on Sep. 28, 2009.

(30) Foreign Application Priority Data

Nov. 7, 2008  (DE) .................. 10 2008 056 346

(51) Int. Cl.
| | |
|---|---|
| *H05B 6/02* | (2006.01) |
| *A61L 2/12* | (2006.01) |
| *A61L 2/22* | (2006.01) |
| *B29C 49/42* | (2006.01) |
| *B29C 49/06* | (2006.01) |
| *B29C 49/12* | (2006.01) |
| *B29C 49/36* | (2006.01) |
| *B29C 49/64* | (2006.01) |
| *B29C 35/08* | (2006.01) |

(52) U.S. Cl.
CPC ... *A61L 2/12* (2013.01); *A61L 2/22* (2013.01); *B29C 49/42* (2013.01); *A61L 2202/23* (2013.01); *B29C 49/06* (2013.01); *B29C 49/12* (2013.01); *B29C 49/36* (2013.01); *B29C 49/64* (2013.01); *B29C 2035/0855* (2013.01)

(58) Field of Classification Search
CPC ...... A61L 2/00; B29C 49/28; B29C 49/4205; B29C 49/4221
USPC ........ 264/457, 454, 37.14, 37.25, 37.31, 534, 264/535, 410, 417, 420, 432, 458, 462, 473, 264/474, 476, 479–481, 488–489, 492, 532, 264/289.3, 291
See application file for complete search history.

(56) References Cited

U.S. PATENT DOCUMENTS

| | | |
|---|---|---|
| 6,562,281 B1 | 5/2003 | Marchau et al. |
| 6,692,684 B1 * | 2/2004 | Nantin et al. .................. 264/521 |
| 6,984,360 B1 | 1/2006 | Feuilloley et al. .............. 422/28 |
| 7,900,422 B2 | 3/2011 | Fischer ............................ 53/426 |

(Continued)

FOREIGN PATENT DOCUMENTS

| | | |
|---|---|---|
| CN | 1812817 | 8/2008 |
| DE | 2908086 A1 | 9/1980 |
| DE | WO2008055685 * | 5/2008 |
| EP | 0996530 | 5/2000 |
| EP | 1 056 481 B1 | 12/2000 |
| JP | 04 04 49 02 A | 2/1992 |
| WO | WO 2007/131701 A2 | 11/2007 |
| WO | WO 2007/140883 A2 | 12/2007 |
| WO | WO 2008/055685 A1 | 5/2008 |

*Primary Examiner* — Stella Yi
(74) *Attorney, Agent, or Firm* — Simmons Perrine Moyer Bergman PLC

(57) ABSTRACT

A method for pre-treating preforms (12) made of thermoplastic plastic, before they are shaped into containers (13) by means of a stretch blow molding process and filled with liquid. The preforms (12) are tempered and sterilized for the subsequent stretch blow molding process. Tempering of the preforms (12) is carried out by means of microwave radiation and by sterilization of the preforms (12) during the pre-treatment.

28 Claims, 5 Drawing Sheets

(56) References Cited

U.S. PATENT DOCUMENTS

| | | |
|---|---|---|
| 2005/0118057 A1 | 6/2005 | Quetel et al. |
| 2006/0120914 A1 | 6/2006 | Salda |
| 2008/0152538 A1* | 6/2008 | Quetel et al. .................... 422/28 |
| 2009/0293429 A1 | 12/2009 | Till ................................ 53/425 |
| 2010/0052224 A1 | 3/2010 | Humele et al. ................ 264/489 |

* cited by examiner

METHOD FOR PRE-TREATING PREFORMS AND BLOW MOLDING APPARATUS FOR PRE-TREATING AND BLOW MOLDING PREFORMS INTO CONTAINERS

This is a continuation of prior International Application PCT/EP2009/062532, filed Sep. 28, 2009, which claims priority to German Patent Application DE 10 2008 056 346.3, filed Nov. 7, 2008, the entire disclosures of which are hereby incorporated by reference herein.

The present invention relates to a method for pre-treating preforms. The invention furthermore relates to a blow molding apparatus for pre-treating and blow molding preforms into containers.

BACKGROUND

When producing beverage containers in a blow molding process, the so called preforms are first heated to an adequate temperature. The preforms are then fixed in blow molds and transformed into the desired container shape by controlled injection of air. Only when they have the desired container shape, they have the necessary volume to be filled with liquid. The containers usually have to be sterilized before filling to guarantee a long shelf life of the bottled liquid. With sufficient sterilization the addition of preservatives in beverages can be reduced.

Methods have been developed whereby the preforms are sterilized after tempering and before blow molding. These methods have been developed due to increasingly higher demands on the cleanness of the containers and due to the desired minimization of preservatives in beverages. Thereby a largely sterile process up to filling can be achieved and maintained.

EP 1 056 481 B1 describes a method for sterilizing hollow bodies, whereby a vaporized sterilizing medium is applied on the surfaces to be sterilized. The evaporation of the sterilizing agent is done outside the hollow body close to its opening. The sterilizing agent is introduced to and aspired from the inside of the hollow body, thereby generating a gas stream that distributes the agent to all surface areas. The hollow body can either be already in the shape of a beverage container or it can be a preform which is then blow molded into a beverage container.

JP 04 04 49 02 A describes a method for the sterilization of preforms before they are tempered and blow molded into the desired shape of a beverage container.

It has been customary to heat the preforms to the required temperature for blow molding by means of hot air and/or by infrared radiation. From WO 2007/131701 A2 a heating device for plastic preforms is known that uses microwave radiation.

SUMMARY OF THE INVENTION

It is an object of the present invention to provide a fast and simple heating of the preforms, as well as a related sterilization of these in order to achieve a largely closed process for the subsequent transformation of the preforms into containers and their filling with liquid.

The present invention provides a method for pre-treating preforms of thermoplastic synthetic material, before they are formed into containers by means of a stretch blow molding process and filled with liquid. In this method the preforms are tempered and sterilized for the subsequent blow molding process. The tempering or heating of the preforms is done by microwave radiation. The sterilization of the preforms is preferably performed during radiation by the introduction of liquid and/or gaseous sterilizing medium into the preforms.

According to a preferred embodiment of the invention the container is produced by a stretch blow molding process in a stretch blow molding apparatus. The difference between a stretch blow molding apparatus and a blow molding apparatus is that the stretch blow molding apparatus comprises an additional so called stretching rod, which stretches the container in the axial direction simultaneously to the blowing process. This gives the final container a biaxial orientation which leads to an improved stability of the container. This is especially advantageous for containers to be filled with carbonated beverages.

It is particularly advantageous when the sterilization of the preforms is done during and/or immediately after the microwave radiation. This allows a continuous and automatic process in which the tempering and sterilization of the containers may take place simultaneously or overlapping in time. It is already known that the preforms can be heated by microwave radiation to the suitable temperature required for the stretch blowing process. In connection with the present invention it has now been recognized that the introduction of a suitable fluid, gas, liquid or gas-liquid-mixture can be advantageous in terms of interaction of microwave radiation with the thermoplastic material of the preforms. This effect can be used advantageously to sterilize the preforms already during tempering. A suitable liquid sterilizing medium can be used with certain characteristics as subsequently described. The fluid must be able to activate the microwave radiation and enhance the sterilizing effect. The fluid is introduced into the preforms where it can interact with the microwaves advantageously, enhancing the effect of the radiation. This can furthermore lead to an improved heating effect, especially and/or the preforms can be heated to the required temperature with a lesser radiation intensity.

Liquid and/or gaseous hydrogen peroxide ($H_2O_2$), peracetic acid or the like can be used as sterilizing medium. The sterilizing medium can be introduced into the preform as liquid and/or in a gaseous form. A mixture of hot air and hydrogen peroxide, peracetic acid or the like can be used as sterilizing medium. Basically, other sterilization media which show the same effect can also be used. It is advantageous if the sterilizing medium shows the desired interaction with the microwave radiation. Thereby the radiation can be more efficiently used and/or the heating of the preforms is improved.

According to a preferred embodiment of the inventive method the sterilizing medium is introduced into each preform by at least one nozzle. This can be done quickly and the sterilizing medium gets distributed homogeneously in the preform, especially on the inner surface of the preform. The nozzle is preferentially arranged in the holder or retaining thorn for the preforms. Furthermore an additional aspiration unit can be provided so that after the introduction of the sterilizing medium into the preforms and the heating by radiation, the sterilizing medium can be aspirated out of the preforms quickly and completely.

It is of further advantage if the sterilizing medium is vaporized by the microwave radiation and develops its sterilizing effect on the inner surface of the preforms. After sterilization and during or after tempering the preforms can be rinsed with a suitable washing medium to remove any traces of the sterilizing medium.

The tempering and sterilization of the preforms is preferably done in a continuous process, especially on a rotary machine.

The present invention furthermore comprises a stretch blow molding apparatus for the pre-treatment and stretch blow molding of preforms made of thermoplastic plastic into containers. The apparatus comprises handling means for handling and continually treating and transporting preforms, a tempering unit for heating the preforms and a sterilization unit, whereby the tempering unit comprises a microwave radiation unit. The sterilization unit is at least partially integrated in the handling means, so that the sterilization of the containers can be done in the context and/or in an advantageous combination with the microwave radiation leading to a warming of the preforms.

An advantageous embodiment of the stretch blow molding apparatus according to the invention has handling means that each comprise retaining thorns for holding the preforms in their neck region. The retaining thorns have nozzles for the introduction of the sterilizing medium into the preforms. The nozzles of the retaining thorns can each comprise inlet and/or outlet pipes for the sterilizing medium that can be aspired after the treatment via the nozzles or other suitable aspiration devices.

The apparatus according to the invention can especially be a rotary apparatus, whereby the preforms are continuously transformed into sterilized containers.

The term preform used in the present context generally means a pre-product of containers, especially beverage containers. Preforms are sometimes also called blanks. Blanks are unilaterally closed tubes having an open end with a neck region, with which they are placed in a form to be formed into containers by stretch blow molding. The preforms are made of a suitable thermoplastic plastic, for instance PET (Polyethylene).

BRIEF DESCRIPTION OF THE DRAWINGS

In the following passages, the attached figures further illustrate exemplary embodiments of the invention and their advantages. The size ratios of the individual elements in the figures do not necessarily reflect the real size ratios. It is to be understood that in some instances various aspects of the invention may be shown exaggerated or enlarged to facilitate an understanding of the invention.

DETAILED DESCRIPTION

Figure 1:
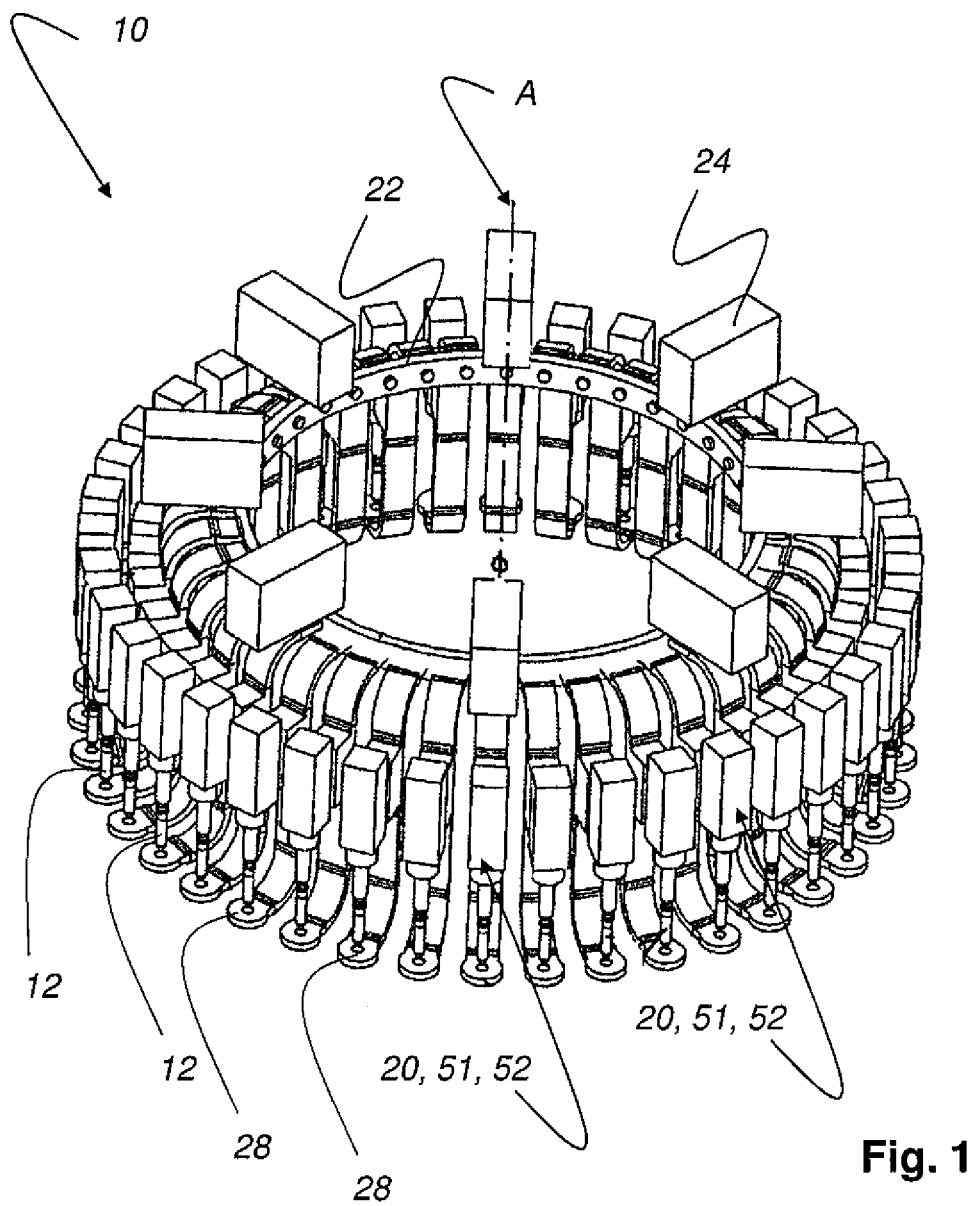
FIG. 1 shows a schematic representation of a tempering and sterilization unit.

The schematic representation of FIG. 1 shows a handling apparatus 10 for the treatment of preforms 12. The handling apparatus 10 comprises a tempering unit 51 and a sterilization unit 52 that are integrated in single treatment stations 20. In this method the preforms 12 are treated in a continuous process, whereby the preforms can be moved on a circular path through the tempering unit 51 during heating and simultaneously be sterilized by the sterilization unit 52. The treatment stations 20 are mounted together on a carrier 22. On the carrier 22 further components can be attached; e.g. eight microwave radiation units 24 are attached in this embodiment. The functions of such a unit are described in WO 2007/131701 A2. The tempering units 51 are connected to the microwave radiation units 24 and together they run around the axis A of the apparatus and the sterilization unit 52 during the treatment of the preforms 12.

As has already been described, the preform 12 is heated to the required temperature by means of the tempering unit 51 and the microwave radiation unit 24. To get a uniform heating of the preforms 12, the preforms 12 are pushed through a resonator 28, which is connected with the tempering unit 51. The sterilization of the preforms 12 is done with a sterilization unit 52 that is at least partially integrated in the handling apparatus 10 in relation and/or in an advantageous combination with the microwave radiation unit 24 leading to a warming of the preforms 12.

The handing over of the preforms 12 to the handling apparatus 10 can be done by means of a device located upstream, for example a star, especially a saw tooth star or clamping star.

Figure 2:
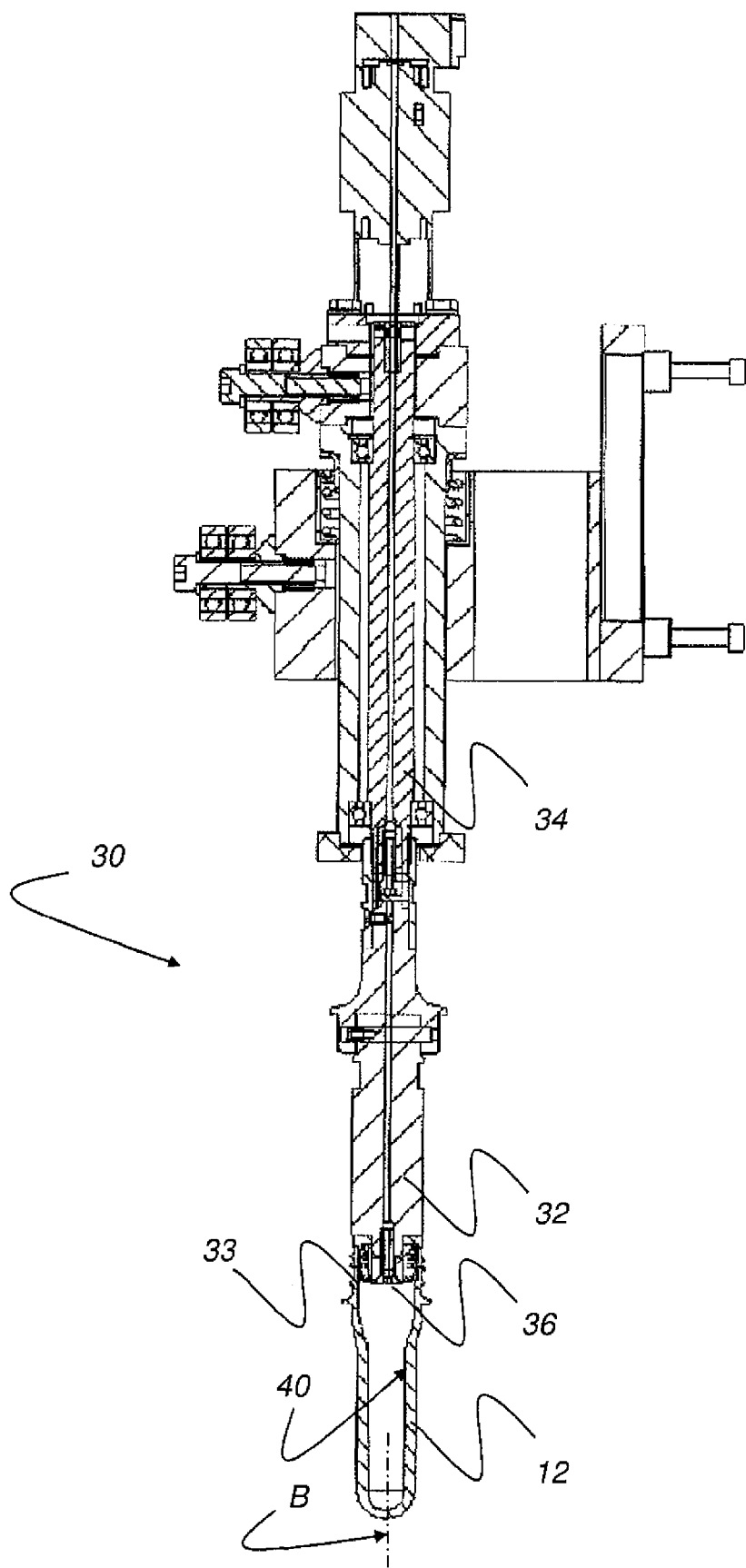
FIG. 2 shows a cross section of a handling unit for a preform.

FIG. 2 shows a cross section of a handling unit 30 for a preform 12. The handling unit 30 comprises a preform retaining unit 32 and a driving unit 34. In the shown embodiment the preform retaining unit 32 is designed as a retaining thorn, which reaches into the opening of the neck region 33 of the preform 12 thereby retaining it. The driving unit 34 is preferentially a drive that fulfills all motion requirements. First of all a lowering motion is necessary, which introduces the preform 12 along its longitudinal axis B into the resonator 28 (shown in FIG. 1) from above. On the other hand a controlled lifting is necessary to lift out the preform 12 along its longitudinal axis 13 from the resonator 28 (shown in FIG. 1). The preform retaining unit 32 furthermore comprises a nozzle 36 that serves for the introduction of liquid and/or gaseous sterilizing medium into the preform 12. The sterilizing medium is introduced into the preform 12 during radiation with microwaves and evaporates when the preform 12 is heated. The sterilizing medium thus develops its sterilizing effect on the surface 40 of the preform 12. In the shown embodiment the sterilization unit 52 is connected to the handling unit 30 and to the tempering unit 51 at the same time. Optionally the sterilization can also be performed after the heating of the preform 12.

Figure 3:
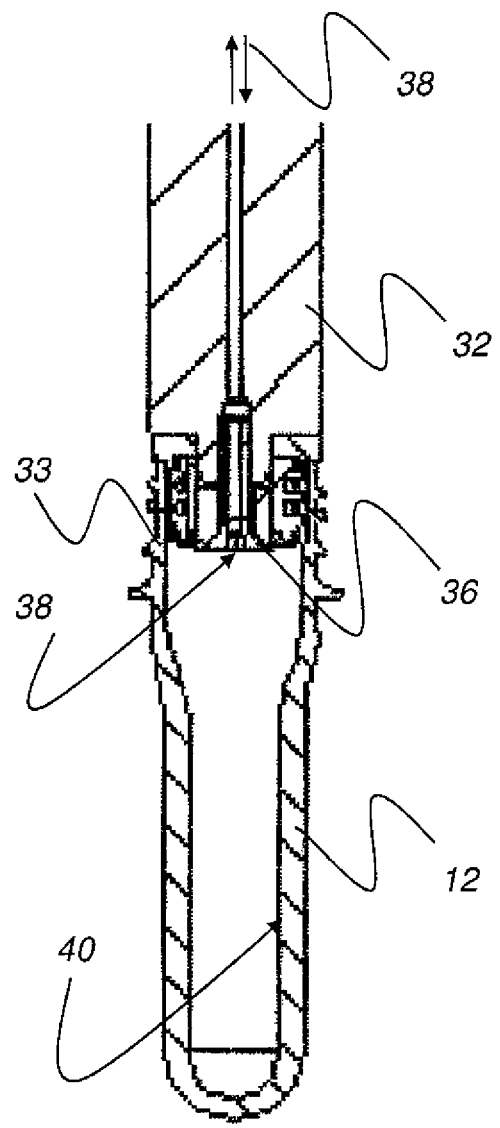
FIG. 3 shows an enlarged part of the handling unit for a preform according to FIG. 3.

FIG. 3 shows an enlarged section of a sterilization unit 52 for a preform 12 according to FIG. 2. FIG. 3 again clearly shows the handling unit 30 for the preform 12. During the pre-treatment the preform 12 is held by the preform retaining unit 32, which enters the opening in the neck region 33 of the preform 12. The nozzle 36 comprises inlet and/or outlet pipes, through which the sterilizing medium is fed into and aspired from the preforms 12, whereby the sterilizing medium develops its sterilizing effect on the surface of the preforms 12 through additional heating.

Figure 4:
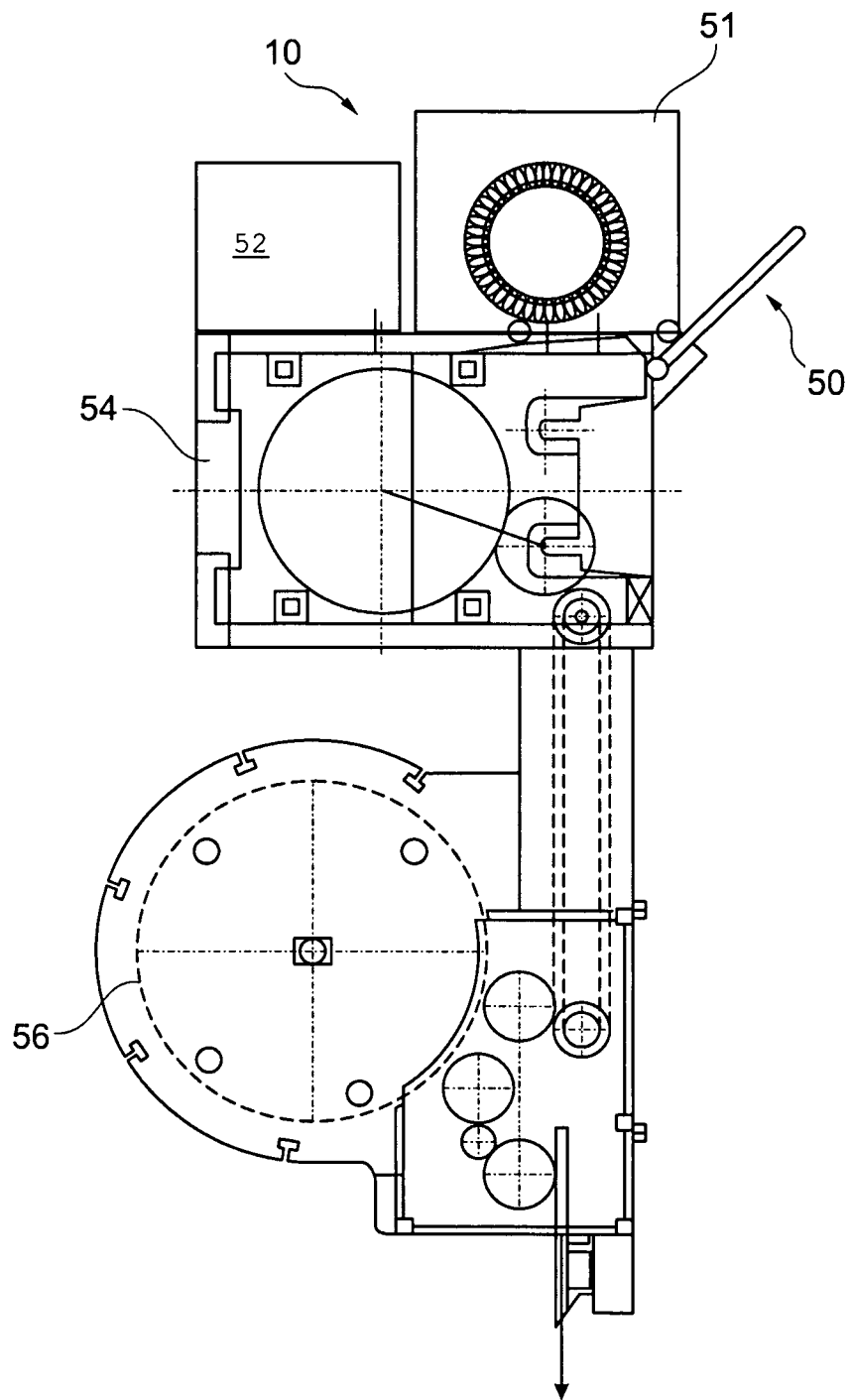
FIG. 4 shows a top view of an apparatus for the production of containers.

FIG. 4 shows another embodiment of the arrangement of the treatment stations and of the apparatus for the production of containers. The preforms 12 are handed over to the handling apparatus 10 by means of a feeder 50. The preforms 12 are handed over to individual tempering units 51 connected to a microwave radiation unit 24. The preforms 12 are heated to the required temperature by microwave radiation and immediately handed over to a sterilization unit 52 located downstream. In the sterilization unit 52 the preforms 12 are sterilized and rinsed if necessary. Subsequently the pre-treated preforms 12 are transferred to a stretch blow molding machine 54 by an arrangement of transport stars. In the stretch blow molding machine 54 the preforms 12 are shaped into finished containers. After the production of the containers they can be transferred to a filling apparatus 56 and subsequently to a capping unit and/or a labeling machine.

Figure 5:
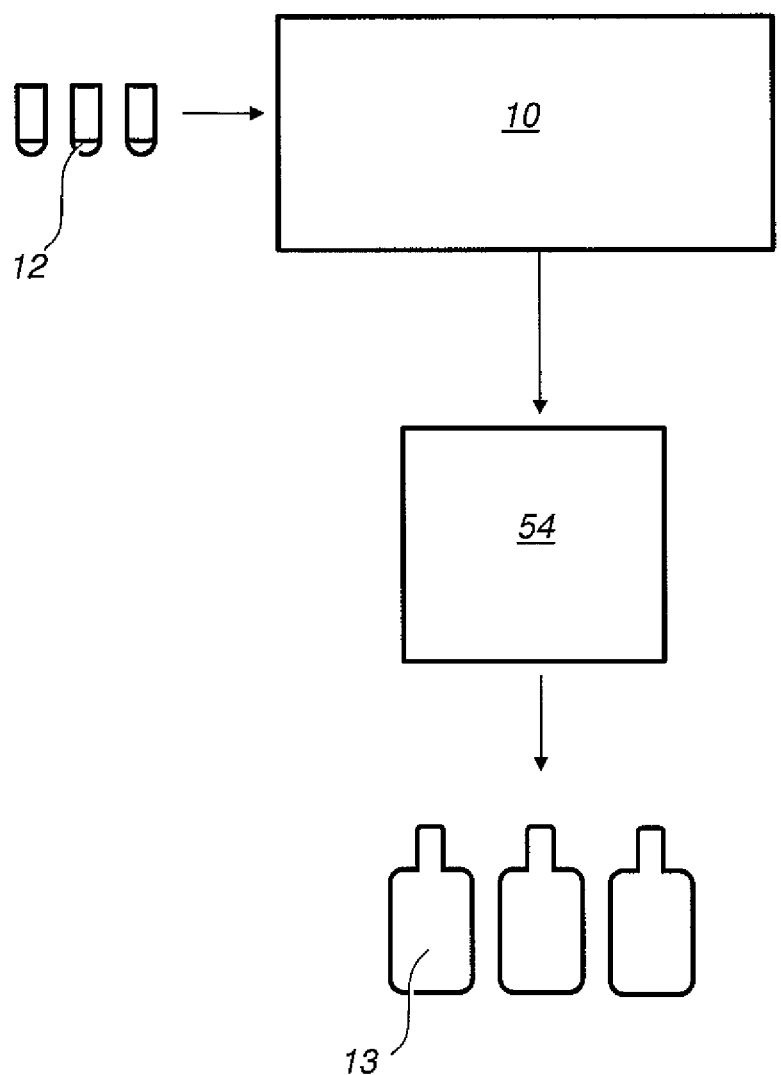
FIG. 5 shows a schematic representation of an apparatus for the production of containers.

FIG. 5 shows a schematic representation of an apparatus for the production of containers 13. The preforms 12 are tempered and sterilized in a handling apparatus 12. Then they are handed over to a stretch blow molding device 54. There the pre-treated preforms 12 are formed into containers 13 of the desired shape.

The invention has been described with reference to a preferred embodiment. Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method for pre-treating preforms of thermoplastic synthetic material, before the preforms are formed into containers by a blow molding process, comprising:
    tempering and sterilizing the preforms for the blow molding process, a handling unit handling the preforms during the tempering by a tempering unit, a sterilization unit performing the sterilization being integrated at least partially in the handling unit, the preforms being transported by the handling unit, the handling unit including retaining thorns, each retaining thorn for holding a respective preform in a preform neck region, and each retaining thorn having at least one pipe for introduction of sterilizing medium into the respective preform, the pipe being arranged in the retaining thorn holding the respective preform.

2. The method as recited in claim 1, wherein the preforms are sterilized by introduction of the sterilizing medium into the preforms, the sterilizing medium being liquid and/or gaseous.

3. The method as recited in claim 1, wherein the sterilization of the preforms is performed before and/or during and/or immediately following radiation with microwaves.

4. The method as recited in claim 1, wherein liquid and/or gaseous hydrogen peroxide or peracetic acid is used as the sterilizing medium.

5. The method as recited in claim 1, wherein a mixture of hot air and hydrogen peroxide or peracetic acid is used as the sterilizing medium.

6. The method as recited in claim 1, wherein the sterilizing medium is introduced into the preform with at least one nozzle.

7. The method as recited in claim 1, wherein the sterilizing medium is vaporized by microwave radiation and develops a sterilizing effect on a surface of the preforms.

8. The method as recited in claim 1, further comprising rinsing the preforms with a washing medium to remove remaining sterilizing medium after the sterilizing.

9. The method as recited in claim 1, wherein the tempering and sterilizing of the preforms is done in a continuous process.

10. The method as recited in claim 9, wherein the continuous process is on a rotary machine.

11. A method for pre-treating preforms of thermoplastic synthetic material, before the preforms are formed into containers by a blow molding process and filled with liquid, the method comprising: tempering and sterilizing the preforms for the blow molding process, the preforms being treated in a continuous process, a sterilizing unit performing the sterilizing being at least partially integrated into a tempering unit performing the tempering, the sterilizing unit and the tempering unit integrated in single treatment stations, the sterilizing unit and tempering unit mounted together on a moving carrier capable of attaching further components, wherein the tempering and the sterilizing of the respective preform occur at a same time, wherein the sterilizing unit together with the tempering unit and the preforms run around a common axis, and wherein the preforms are handled by a handling device with retainers for holding the preforms in a neck region, the retainers having nozzles for introducing a sterilizing medium into the preforms.

12. The method as recited in claim 11, wherein the tempering is performed by radiation.

13. The method as recited in claim 12, wherein the radiation is microwave radiation.

14. The method as recited in claim 13, wherein the further components include microwave radiation units.

15. The method as recited in claim 11, wherein the preforms move in a circular path.

16. The method as recited in claim 11, wherein the preforms pass through a resonator.

17. The method as recited in claim 11, wherein the sterilization is performed by introduction of a liquid and/or gaseous medium into the preforms.

18. The method as recited in claim 11, wherein the sterilizing is performed during and/or immediately after a tempering of the preforms by microwave radiation.

19. The method as recited in claim 18, wherein the sterilizing and tempering is performed simultaneously or overlapping in time in a continuous and automatic process.

20. The method as recited in claim 17, wherein the medium is hydrogen peroxide.

21. The method as recited in claim 11, wherein the sterilization is performed after the tempering.

22. The method as recited in claim 11, further comprising steps of: shaping the preforms into finished containers, and transferring the containers to a filling apparatus and subsequently to a capping and/or labeling machine.

23. A method for pre-treating preforms of thermoplastic synthetic material, before the preforms are formed into containers by a blow molding process, comprising:
    tempering and sterilizing the preforms for the blow molding process, a preform retaining unit retaining the preforms during the tempering, sterilizing medium being introduced into the preform via a hole in the preform retaining unit, wherein the retaining unit is a retaining thorn and wherein an integrated section of a sterilization unit moves together with a handling unit, wherein the tempering and the sterilizing of the respective preform occur at a same time, wherein the sterilizing unit together with the preform and the retaining thorn run around a common axis A.

24. The method as recited in claim 1, wherein an integrated section of the sterilization unit moves together with the handling unit.

25. A method for pre-treating preforms of thermoplastic synthetic material, before the preforms are formed into containers by a blow molding process, comprising:
    tempering and sterilizing the preforms for the blow molding process, the tempering of the preforms being performed by microwave radiation and the sterilization of the preforms by introduction of a liquid and/or gaseous sterilization medium into the preforms, the sterilization of the preforms occurring before and/or during the tempering by microwave radiation, the sterilization medium being vaporized by the microwave radiation.

26. A method for pre-treating preforms of thermoplastic synthetic material, before the preforms are formed into containers by a blow molding process, comprising:
    tempering and sterilizing the preforms for the blow molding process, a handling unit handling the preforms during the tempering by a tempering unit, a sterilization unit performing the sterilization being integrated at least partially in the handling unit, the preforms being transported by the handling unit, the handling unit including retaining thorns, each retaining thorn for holding a respective preform in a preform neck region, and each retaining thorn having at least one pipe for introduction of sterilizing medium into the respective preform, and aspiring the sterilizing medium from the respective preform.

27. The method as recited in claim 26, wherein the at least one pipe performs the aspiration.

28. A method for pre-treating preforms of thermoplastic synthetic material, before the preforms are formed into containers by a blow molding process, comprising:

tempering and sterilizing the preforms for the blow molding process, a handling unit handling the preforms during the tempering by a tempering unit, a sterilization unit performing the sterilization being integrated at least partially in the handling unit, the preforms being transported by the handling unit, the handling unit including retaining thorns, each retaining thorn fitting into and holding a respective preform in a preform neck region, and each retaining thorn having at least one pipe for introduction of sterilizing medium into the respective preform, the at least one pipe also aspiring the sterilizing medium from the respective preform.

\* \* \* \* \*